United States Patent [19]

Ohmori et al.

[11] Patent Number: 4,544,720
[45] Date of Patent: Oct. 1, 1985

[54] FLUORINE-CONTAINING COPOLYMER

[75] Inventors: Akira Ohmori, Ibaraki; Nobuyuki Tomihashi, Takatsuki; Hiroshi Inukai; Yoshiki Shimizu, both of Settsu, all of Japan

[73] Assignee: Daikin Kogyo Co., Ltd., Osaka, Japan

[21] Appl. No.: 653,005

[22] Filed: Sep. 21, 1984

[30] Foreign Application Priority Data

Sep. 21, 1983 [JP] Japan .................................. 58-175123

[51] Int. Cl.⁴ .................... C08F 214/18; C08F 214/26
[52] U.S. Cl. .................................. 526/247; 526/242; 526/249
[58] Field of Search .......................... 526/242, 247, 249

[56] References Cited

U.S. PATENT DOCUMENTS 3,366,610 1/1968 Anderson .......................... 526/247
3,414,634 12/1968 Sorkin ................................. 526/247
3,654,245 4/1972 Kometani et al. ................. 526/242

*Primary Examiner*—Harry Wong, Jr.
*Attorney, Agent, or Firm*—Armstrong, Nikaido, Marmelstein & Kubovcik

[57] ABSTRACT

A novel fluorine-containing copolymer having functional groups comprising structural units of 1,1-difluoroethylene and structural units of a monomeric compound of the formula:

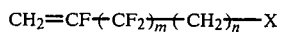

wherein X is —OH,

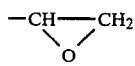

or —COOH group, m is 0 or an integer of 1 to 10 and n is an integer of 1 to 4, which may futher contain structural units of at least one monomer selected from the group consisting of tetrafluoroethylene, chlorotrifluoroethylene, monofluoroethylene 1,1,2-trifluoroethylene, hexafluoropropene and a fluoroalkyl vinyl ether. The copolymer is curable at room temperature, and is useful as a material for fluorine-containing rubbers, molded articles and paints.

2 Claims, No Drawings

FLUORINE-CONTAINING COPOLYMER

BACKGROUND OF THE INVENTION

The present invention relates to novel fluorine-containing copolymers having functional groups, and more particularly to the fluorine-containing copolymers useful, for instance, as fluorine-containing rubbers, molding materials and room temperature curing paint materials.

Fluorine-containing polymers have been employed for various purposes such as fluoro-rubbers, molding materials and coating materials. Fluoro-resin paints are excellent in chemical resistance, weatherability, stain resistance and heat resistance, but require baking at high temperatures. In recent years, room temperature curing fluoro-resin paints which do not require baking at high temperatures have been proposed. For instance, it is proposed to use copolymers of fluoroolefin, cyclohexyl vinyl ether and other comonomers as room temperature curing paint materials (Japanese Unexamined Patent Publication No. 55-25414, No. 57-34107 and No. 57-34108). In general, room temperature curing paints are incorporated with a methyl methacrylate polymer to raise the transparency of coatings. The proposed copolymers have the defect of being poor in compatibility with the methyl methacrylate polymer.

It is an object of the present invention to provide a novel fluorine-containing copolymer having functional groups.

A further object of the invention is to provide a fluorine-containing copolymer useful as a material for fluorine-containing rubber, molded article and paint.

A still further object of the invention is to provide a fluorine-containing copolymer useful as a material for room temperature curing paints and moreover compatible with a methyl methacrylate polymer.

These and other objects of the present invention will become apparent from the description hereinafter.

SUMMARY OF THE INVENTION

In accordance with the present invention, there is provided a fluorine-containing copolymer comprising (a) structural units of the formula:

$$-CH_2-CF_2-$$

and (b) structural units of the formula:

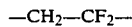
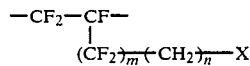

wherein X is —OH,

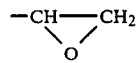

or —COOH group, m is 0 or an integer of 1 to 10 and n is an integer of 1 to 4.

The copolymer of the present invention may further contain at least one kind of structural units selected from the group consisting of (c) $-CF_2-CF_2-$, (d) $-CClF-CF_2-$, (e) $-CH_2-CHF-$, (f) $-CHF-CF_2$, (g)

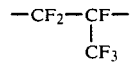

and (h)

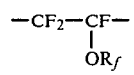

wherein $R_f$ is a fluoroalkyl group.

DETAILED DESCRIPTION

The fluorine-containing copolymers of the present invention are prepared by copolymerizing 1,1-difluoroethylene and a compound having a functional group represented by the formula (I):

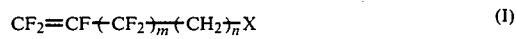

wherein X is —OH,

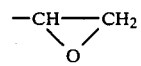

or —COOH group, m is 0 or an integer of 1 to 10 and n is an integer of 1 to 4, or by copolymerizing 1,1-difluoroethylene, the compound (I) and at least one monomer, as the third component, selected from the group consisting of tetrafluoroethylene, chlorotrifluoroethylene, monofluoroethylene, 1,1,2-trifluoroethylene, hexafluoropropene, and a fluoroalkyl vinyl ether, e.g. a fluoroalkyl vinyl ether having a $C_1$ to $C_5$ fluoroalkyl group. 1,1-Difluoroethylene and the compound (I) can be used in any proportions. The amount of the above third component is determined according to the uses of the copolymers of the invention. Other monomers may be further copolymerized with the above monomers so long as the physical properties of the copolymers of the present invention are not impaired.

The copolymers of the present invention usually have a molecular weight of 10,000 to 500,000 measured by gel permeation chromatography and a glass transition temperature of $-40°$ to $70°$ C.

Emulsion polymerization, suspension polymerization and solution polymerization are applied to the preparation of the fluorine-containing copolymers of the present invention. In any of the above polymerization methods, the polymerization is usually carried out at a temperature of 0° to 150° C., preferably 5° to 95° C., and at a pressure of not more than 50 kg/cm²G.

The polymerization mediums are, for instance, water, 1,1,2-trichloro-1,2,2-trifluoroethane, 1,2-dichloro-1,1,2,2-tetrafluoroethane and mixtures thereof for the suspension polymerization, and methyl ethyl ketone, ethyl acetate, butyl acetate and the like for the solution polymerization. Known polymerization initiators can be employed in the present invention. For instance, redox initiators consisting of a persulfate as an oxidizing agent such as ammonium persulfate or potassium persulfate, a reducing agent such as sodium sulfite, and a transition metal salt such as ferrous sulfate are employed in the emulsion polymerization. Azo compounds and organic peroxide compounds are employed in the suspension and solution polymerizations, such as azobisisobutyronitrile, isobutyryl peroxide, octanoyl peroxide and di-isopropyl peroxydicarbonate.

The compounds (I) are novel compounds. The compound of the formula: $CF_2=CF(CF_2)_m(CH_2)_nOH$ wherein m and n are as defined above, is prepared, for instance, by dechlorination or debromination of a compound of the formula:

$$CF_2X^1CFX^2(CF_2)_m(CH_2)_nOH$$

wherein $X^1$ and $X^2$ are the same or different and each is chlorine or bromine, and m and n are as defined above. The dechlorination or debromination is carried out by reacting the above compound with a dehalogenation agent such as zinc, magnesium, tin, sodium or potassium at a temperature of 0° to 150° C., preferably 50° to 100° C., at a pressure of 1 to 10 atms in a reaction solvent such as water, dimethylformamide, methanol or acetone. The compound $CF_2X^1CFX^2(CF_2)_m(CH_2)_nOH$ can be prepared by various processes, for instance, by reduction of a compound of the formula: $CF_2X^1CFX^2CF_2COOR$ wherein $X^1$ and $X^2$ are as defined above and R is a lower aliphatic group or an alicyclic group, or by reduction of a compound of the formula: $CF_2X^1CFX^2(CF_2)_mCH_2CHICH_2OH$ wherein $X^1$, $X^2$ and m are as defined above, prepared by a radical reaction of allyl alcohol and a compound of the formula: $CF_2X^1CFX^2(CF_2)_mI$ wherein $X^1$, $X^2$ and m are as defined above.

In a like manner, the compound of the formula:

$$CF_2=CF(CF_2)_m(CH_2)_nCH\underset{O}{\overset{}{\diagdown\diagup}}CH_2$$

wherein m and n are as defined above, is prepared, for instance, by dechlorination or debromination of a compound of the formula:

$$CF_2X^1CFX^2(CF_2)_m(CH_2)_nCH\underset{O}{\overset{}{\diagdown\diagup}}CH_2$$

wherein $X^1$, $X^2$, m and n are as defined above. The compound of the formula: $CF_2=CF(CF_2)_m(CH_2)_nCOOH$ wherein m and n are as defined, is prepared, for instance, by dechlorination or debromination of a compound of the formula:

$$CF_2X^1CFX^2(CF_2)_m(CH_2)_nCOCl$$

wherein $X^1$, $X^2$, m and n are as defined above, followed by reaction with water. Representative examples are shown below.

(i)
$$CF_2ClCFClI \xrightarrow{CH_2=CHCH_2OH}$$

$$CF_2ClCFClCH_2\underset{OH}{\overset{}{C}}HCH_2I \xrightarrow{NaOH}$$

$$CF_2ClCFClCH_2CH\underset{O}{\overset{}{\diagdown\diagup}}CH_2 \xrightarrow{\text{dehalogenation agent (e.g. Zn)}}$$

$$CF_2=CFCH_2CH\underset{O}{\overset{}{\diagdown\diagup}}CH_2$$

(ii)
$$CF_2ClCFClCF_2CCl_3 \xrightarrow{SO_3}$$

$$CF_2ClCFClCF_2COCl \xrightarrow{\text{dehalogenation agent (e.g. Zn)}}$$

$$CF_2=CFCF_2COCl \xrightarrow{H_2O} CF_2=CFCF_2COOH$$

The fluorine-containing copolymers of the present invention can be used for various purposes, e.g. fluororubbers, molding materials and coating materials. The copolymers of the invention are curable with a curing agent at room temperature, and are particularly useful for room temperature curing paints.

In case that the copolymers of the invention are used in room temperature curing paints, it is preferable that the copolymers contain (1) 50 to 99% by mole of 1,1-difluoroethylene, (2) 1 to 50% by mole of the compound (I) having a functional group, and (3) 0 to 30% by mole of tetrafluoroethylene or chlorotrifluoroethylene as a third component. When the component (3) is used, a part of the component (1) and/or the component (2) is replaced therewith. In that case, the component (3) is employed in an amount of at least 0.1% by mole, especially at least 0.5% by mole. The copolymers having a 1,1-difluoroethylene content of at least 50% by mole are good in chemical resistance, weatherability and stain resistance of the paint films. The copolymers having a content of the compound (I) of 1 to 50% by mole are good in copolymerizability upon the preparation thereof and curability when used in paints. The use of tetrafluoroethylene or chlorotrifluoroethylene is effective in improving the solubility in solvents of the produced copolymers, and they may be employed in such an amount that the hardness of the paint films is not extremely lowered.

The curing agent used for preparing the paints is selected according to the functional group. In case that the functional group is hydroxyl group or carboxyl group, isocyanates are usually employed as a curing agent, e.g. hexamethylene diisocyanate, tolylene diisocyanate and hydrogenated tolylene diisocyanate. The curing agent used for epoxy functional group includes, for instance, polyamines such as xylenediamine and diethylenetriamine. The curing agent reacts with the functional groups of the copolymers to form crosslinkages, thereby hardening the paints at room temperature.

The fluorine-containing copolymers of the present invention have a good compatibility with a methyl methacrylate polymer, and accordingly the methyl methacrylate polymer can be incorporated in the paints without any troubles, if desired. Moreover, the copolymers per se of the invention have an excellent transparency.

The room temperature curing paints containing the copolymers of the invention can be applied as exterior and interior paints to metals, wood, concrete, plastics, etc. in the same manner as usual paints. The films formed from the paints have excellent chemical resistance, weatherability and stain resistance.

When a monomer capable of lowering the glass transition temperature is used in the preparation of the fluorine-containing copolymers of the present invention, the copolymers are also useful as fluororubbers.

The present invention is more specifically described and explained by means of the following Examples, in which all parts are by weight. It is to be understood that the present invention is not limited to the Examples, and various changes and modifications may be made in the invention without departing from the spirit and scope thereof.

REFERENCE EXAMPLE

[Synthesis of $CF_2=CFCH_2CH_2OH$]

(1) A 1 liter autoclave equipped with a stirrer and a thermometer was charged with 1 mole (279 g) of $CF_2ClCFClI$ and 3 g of t-butyl peroxyisobutyrate. After degassing, ethylene was supplied to the autoclave and the reaction was carried out at a temperature of 70° to 80° C., while maintaining the inner pressure at 5 kg/cm$^2$G with supply of ethylene, until no ethylene was consumed. The reaction mixture was taken out and was rectified, thus $CF_2ClCFClCH_2CH_2I$ (boiling point: 68° to 70° C. at 25 mmHg) was obtained in a yield of 96%.

(2) A 1 liter flask equipped with a stirrer and a thermometer was charged with 0.5 mole (151.5 g) of $CF_2ClCFClCH_2CH_2I$ and 1 mole (116.5 g) of chlorosulfonic acid, and the reaction was carried out at 40° C. for 24 hours. The obtained reaction mixture was added dropwise to water, and the bottom oil layer was taken out and rectified to give 82 g of $CF_2ClCFClCH_2CH_2OH$ (yield: 83.7%).

(3) A 1 liter flask equipped with a stirrer, a thermometer, a reflux condenser and a dropping funnel was charged with 300 ml of water and 100 g of zinc, and 0.5 mole (98.5 g) of $CF_2ClCFClCH_2CH_2OH$ was added dropwise to the flask at a temperature of 50° to 60° C. The inner temperature rose to 80° C. by heat generation with start of the reaction. After the completion of the dropwise addition, the reaction was continued at 80° C. for 5 hours. The obtained organic compound was rectified to give $CF_2=CFCH_2CH_2OH$ (boiling point: 93° C. at 760 mmHg). The yield throughout the steps (1) to (3) was 73%.

The obtained product was subjected to nuclear magnetic resonance (NMR) analysis. The results are shown below.

NMR data in which fluorine atom and hydrogen atom are indicated as follows:

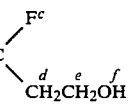

| $^{19}F$ | (external standard: $CF_3COOH$, high magnetic field side: +, hereinafter the same) | |
|---|---|---|
| Fluorine atom | +δ(ppm) | Spin-spin bond (Hz) |

-continued

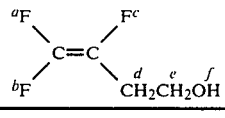

| | | |
|---|---|---|
| a | 26.9 | d, d, t, $J_{gem} = 89$, $J_{cis} = 34$, $J_{F-H} = 2$ |
| b | 47.0 | d, d, t, $J_{trans} = 114$, $J_{gem} = 89$, $J_{F-H} = 4$ |
| c | 97.8 | d, d, t, $J_{cis} = 34$, $J_{trans} = 114$, $J_{F-H} = 21$ |

| $^1H$ | (internal standard: tetramethylsilane, hereinafter the same) | |
|---|---|---|
| Hydrogen atom | δ(ppm) | Spin-spin bond (Hz) |
| d | 2.57 | d, m, $J_{F-H} = 21$ |
| e | 3.83 | t, $J_{H-H} = 7$ |
| f | 4.4 | s |

EXAMPLE 1

A 250 ml autoclave was charged with 50 ml of ethyl acetate, 0.5 g of di-isopropyl peroxydicarbonate and 8.8 g of $CF_2=CFCF_2CH_2OH$. After thoroughly replacing the air in the autoclave with nitrogen, 31.2 g of 1,1-difluoroethylene (hereinafter referred to as "VdF") was added to the autoclave, and the autoclave was placed in a constant temperature oven at 40° C. for 48 hours. The reaction mixture was added to petroleum ether, and the resulting precipitate was dried under reduced pressure to give 15.6 g of a fluorine-containing copolymer.

The copolymer had a molecular distribution ranging from 30,000 to 200,000 (measured by gel permeation chromatography), and an intrinsic viscosity [η] of 0.22 in methyl ethyl ketone. Also, differential scanning calorimetric (DSC) analysis of the copolymer showed a glass transition temperature (Tg) of −23° C. and a thermal decomposition starting temperature (Td) of 297° C.

In $^{19}F$ nuclear magnetic resonance analysis using trifluoroacetic acid as an external standard, the signal for $CF_2$ was observed at δ = −14 to −55 ppm, and the signal for CF was observed at δ = −90 to −100 ppm. Also, the infrared absorption analysis showed absorption bands based on stretching vibration of OH, CH and $CF_2$ at 3,200 to 3,500 cm$^{-1}$, 2,900 to 3,000 cm$^{-1}$ and 1,120 to 1,280 cm$^{-1}$, respectively.

From the results of the elemental analysis and the above $^{19}F$ NMR analysis, it was confirmed that the obtained polymer was a copolymer of VdF and $CF_2=CFCF_2CH_2OH$ in a molar ratio of 9:1.

EXAMPLES 2 to 8

The procedures of Example 1 were repeated except that the monomers shown in Table 1 were used.

The results are shown in Table 1 together with the results of Example 1.

TABLE 1

| Ex. No. | Composition of copolymer (molar ratio) | Intrinsic viscosity | Tg (°C.) | Td (°C.) |
|---|---|---|---|---|
| 1 | VdF/$CF_2=CFCF_2CH_2OH$ (9/1) | 0.22 | −23 | 297 |
| 2 | VdF/$CF_2=CFCF_2CH_2OH$ (7.5/2.5) | 0.21 | −8 | 288 |
| 3 | VdF/3FCl/$CF_2=CFCF_2CH_2OH$ (7/2/1) | 0.22 | −16 | 336 |
| 4 | VdF/TFE/$CF_2=CFCF_2CH_2OH$ (8/1/1) | 0.19 | −12 | 296 |
| 5 | VdF/$CF_2=CFCH_2CH_2OH$ (7/3) | 0.15 | −11 | 262 |
| 6 | VdF/3FCl/$CF_2=CFCH_2CH_2OH$ (7/2/1) | 0.19 | −9 | 300 |
| 7 | VdF/$CF_2=CF(CF_2)_2CH_2CH_2OH$ (9/1) | 0.20 | −21 | 292 |

TABLE 1-continued

| Ex. No. | Composition of copolymer (molar ratio) | Intrinsic viscosity | Tg (°C.) | Td (°C.) |
|---|---|---|---|---|
| 8 | VdF/3FCl/CF$_2$=CFCF$_2$CF$_2$(CH$_2$)$_2$OH (8/1/1) | 0.22 | −17 | 302 |

(Notes)
VdF: CH$_2$=CF$_2$
3FCl: CClF=CF$_2$
TFE: CF$_2$=CF$_2$

Examples 1 to 8 illustrate the preparation of the fluorine-containing copolymers of the invention by solution polymerization. In general, solution polymerization of fluoroolefins is slow in rate. Particularly, when using hydrocarbon solvents, there are instances where the polymerization does not proceed at all. Even if the polymerization proceeds, the produced polymer is poor in solubility in the solvents. For these reasons, solution polymerization has been rarely applied to the polymerization of fluoroolefins.

The fluorine-containing copolymers of the invention can be easily prepared by solution polymerization, and moreover the produced copolymers have a good solubility in solvents, thus the solution polymerization which has been nearly impossible is made possible by the present invention.

The reaction mixture in the form of a solution obtained by the solution polymerization can be directly utilized as room temperature curing paints by incorporating a curing agent into the reaction mixture. In comparison to suspension or emulsion polymerization which requires a post-treatment of the produced copolymer such as isolation and drying, the solution polymerization is advantageous in this respect.

Films having a thickness of 0.2 mm were prepared from the copolymers obtained in Examples 3, 4, 6 and 8, and the light transmittance of the films were measured at the wavelengths shown in Table 2.

The results are shown in Table 2.

TABLE 2

| Ex. | Light transmittance (%) Wavelength (nm) | | | | |
|---|---|---|---|---|---|
| No. | 400 | 500 | 600 | 700 | 800 |
| 3 | 90.8 | 91.6 | 92.1 | 92.0 | 92.1 |
| 4 | 89.5 | 90.0 | 90.6 | 90.7 | 90.5 |
| 6 | 87.0 | 86.5 | 85.5 | 90.1 | 90.2 |
| 8 | 90.5 | 91.8 | 92.3 | 92.4 | 92.5 |

EXAMPLE 9

A 400 ml autoclave was charged with 200 ml of water, 2.53 g of di-isopropyl peroxydicarbonate, 28.5 g of CF$_2$=CFCF$_2$CH$_2$OH and 6 g of Methylcellulose 25 (made by KISHIDA CHEMICAL CO., LTD., viscosity: 20 to 30 cP). After thoroughly replacing the air in the autoclave with nitrogen, 100 g of VdF was added to the autoclave. The polymerization was carried out at 25° C. for 24 hours with agitation. The produced copolymer was isolated and dried at 80° C. under reduced pressure. The yield of the copolymer was 85 g. There was no difference in composition and physical properties between the copolymers obtained in this Example and Example 1.

EXAMPLE 10

A 1 liter autoclave was charged with 250 ml of water, 250 ml of 1,2-dichloro-1,1,2,2-tetrafluoroethane and 15.1 g of CF$_2$=CFCF$_2$CH$_2$OH. After thoroughly replacing the air in the autoclave with nitrogen gas, 34 g of VdF and 3.5 g of chlorotrifluoroethylene (hereinafter referred to as "3FCl") were added to the autoclave. The autoclave was heated to 40° C., and after thoroughly agitating, 1 g of isobutyryl peroxide was added to the autoclave to initiate the polymerization. The polymerization was continued for 24 hours, while supplying VdF and 3FCl in a ratio of 9:1 by mole so as to maintain the polymerization pressure at 8.5 kg/cm$^2$G. The produced copolymer was isolated and dried at 80° C. under reduced pressure. The yield was 85 g.

EXAMPLE 11

A 250 ml autoclave was charged with 50 ml of ethyl acetate, 0.5 g of di-isopropyl peroxydicarbonate and 8.7 g of CF$_2$=CFCF$_2$COOH. After replacing the air in the autoclave with nitrogen gas, 23.9 g of VdF was added to the autoclave. Thereafter, the polymerization was conducted in the same manner as in Example 1 to give 28.4 g of a copolymer.

The obtained copolymer had a molecular weight of 40,000 to 60,000 (measured by GPC), Tg of −20° C. and Td of 256° C.

The $^{19}$F NMR analysis using trifluoroacetic acid as an external standard showed a signal based on F of F-C- at −110 to −120 ppm, and the infrared absorption analysis showed an absorption band based on —COOH at 2,500 to 3,500 cm$^{-1}$.

From the NMR and elemental analyses, it was found that the obtained copolymer had a composition of VdF/CF$_2$=CFCF$_2$COOH=9/1 by mole.

EXAMPLE 12

Polymerization of 8.9 g of CF$_2$=CFCF$_2$COOH, 26.3 g of VdF and 2.5 g of 3FCl was carried out in the same manner as in Example 1, to give 28.2 g of a ternary copolymer having a composition of VdF/3FCl/CF$_2$=CFCF$_2$COOH=82/7/11 by mole. The copolymer had an intrinsic viscosity of 0.15, Tg of −13° C. and Td of 280° C.

EXAMPLE 13

A 250 ml autoclave was charged with 50 ml of ethyl acetate, di-isopropyl peroxydicarbonate and 5 g of

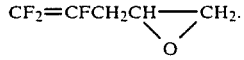

After replacing the air in the autoclave with nitrogen, 30 g of VdF was added to the autoclave and the polymerization was carried out at 40° C. for 24 hours. The yield of a copolymer was 13 g.

The infrared absorption spectrum of the copolymer showed an absorption based on symmetric stretching vibration of epoxy group at 1,250 cm$^{-1}$ and an absorption based on CH stretching vibration of epoxy group at 2,950 to 3,100 cm$^{-1}$.

EXAMPLE 14

In 100 parts of methyl isobutyl ketone was dissolved 100 parts of the fluorine-containing copolymer obtained in Example 3. To the solution was added 20 parts of hexamethylene diisocyanate trimer as a curing agent, and it was sufficiently admixed.

The obtained solution was coated on a defatted aluminum plate having a thickness of 0.2 mm and dried at room temperature for a week. It was observed by the naked eye that the obtained film had a good transparency, and also the film had a pencil hardness of not less than 2H.

EXAMPLE 15

In 100 parts of methyl isobutyl ketone was dissolved 100 parts of the fluorine-containing copolymer obtained in Example 10. The obtained solution was admixed with a solution of 100 parts of an acrylic resin (methyl methacrylate/hydroxyethyl methacrylate=9/1 by mole, hydroxyl value: 50) dissolved in 100 parts of butyl acetate.

To 100 parts of the above mixed solution was added 15 parts of hexamethylene diisocyanate trimer. After sufficiently admixing, the mixture was coated on an aluminum plate treated according to Japanese Industrial Standard (JIS) A 6063. The thickness of the coating was 35 to 50 $\mu$m.

The coated aluminum plate was allowed to stand at room temperature for a week to cure the copolymer, and then subjected to an accelerated weathering test for 4,000 hours by using a super long life carbon arc weathering machine made by Suga Shikenki Kabushiki Kaisha (rain cycle: 18 min./120 min.). The gloss retention based on 60° specular gloss measured according to JIS K 5400 was 85% and very excellent. The gloss retention of a film formed from only the above acrylic resin simultaneously tested was as low as 20%, thus the weatherability was bad.

In addition to the ingredients used in the Examples, other ingredients can be used in the Examples as set forth in the specification to obtain substantially the same results.

What we claim is:

1. A fluorine-containing copolymer comprising (a) 50–99 mole % of structural units of the formula:

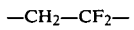

and (b) 1–50 mole % of structural units of the formula:

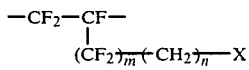

wherein X is —OH, or

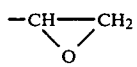

m is 0 or an integer of 1 to 10 and n is an integer of 1 to 4, said copolymer having a molecular weight of 10,000–500,000 and a glass transition temperature of −40° C. to 70° C.

2. The copolymer of claim 1, further comprising 0.1–30 mole % of at least one structural unit selected from the group consisting of —CF$_2$—CF$_2$—, —CClF—CF$_2$—, —CH$_2$—CHF—, —CHF—CF$_2$—, —CF$_2$—CF(CF$_3$)— and —CF$_2$—CF(OR$_f$)— wherein R$_f$ is a fluoroalkyl group.

* * * * *

UNITED STATES PATENT AND TRADEMARK OFFICE
CERTIFICATE OF CORRECTION

PATENT NO. : 4,544,720
DATED : October 1, 1985
INVENTOR(S) : Akira OHMORI et al

It is certified that error appears in the above-identified patent and that said Letters Patent is hereby corrected as shown below:

On the cover page, Item [57], the first formula in the Abstract, change "$CH_2=CF-$" to -- $CF_2=CF-$ --.

Signed and Sealed this

Nineteenth Day of August 1986

[SEAL]

Attest:

*Attesting Officer*

DONALD J. QUIGG

*Commissioner of Patents and Trademarks*